(12) United States Patent
Cao et al.

(10) Patent No.: US 10,989,820 B2
(45) Date of Patent: *Apr. 27, 2021

(54) RADIATION DETECTOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 210 days.

This patent is subject to a terminal disclaimer.

(21) Appl. No.: 16/185,341

(22) Filed: Nov. 9, 2018

(65) Prior Publication Data

US 2019/0094393 A1 Mar. 28, 2019

Related U.S. Application Data

(63) Continuation of application No. PCT/CN2017/072175, filed on Jan. 23, 2017.

(51) Int. Cl.
*G01T 1/24* (2006.01)
*A61B 6/00* (2006.01)
(Continued)

(52) U.S. Cl.
CPC .............. *G01T 1/241* (2013.01); *A61B 6/032* (2013.01); *A61B 6/4208* (2013.01);
(Continued)

(58) Field of Classification Search
CPC ........ G01T 1/241; A61B 6/032; A61B 6/4208
See application file for complete search history.

(56) References Cited

U.S. PATENT DOCUMENTS

| 8,053,722 B1 | 11/2011 | Asghari et al. |
| 10,061,038 B2 * | 8/2018 | Cao .................... G01T 1/244 |

(Continued)

FOREIGN PATENT DOCUMENTS

| CN | 102135626 A | 7/2011 |
| CN | 103430533 A | 12/2013 |

(Continued)

*Primary Examiner* — Hugh Maupin
(74) *Attorney, Agent, or Firm* — IPro, PLLC

(57) ABSTRACT

Disclosed herein is a radiation detector, comprising: a radiation absorption layer comprising an electrode; a voltage comparator that compares a voltage of the electrode to a first threshold; a counter that registers a number of photons of radiation absorbed by the radiation absorption layer; a controller; and a voltmeter. The controller is configured to start a time delay from a time at which the voltage comparator determines that an absolute value of the voltage equals or exceeds an absolute value of the first threshold. The controller is configured to cause the voltmeter to measure the voltage upon expiration of the time delay. The controller is configured to determine the number of photons by dividing the voltage measured by the voltmeter by a voltage that a single photon would have caused on the electrode. The controller can cause the number registered by the counter to increase by the number of photons.

20 Claims, 17 Drawing Sheets

(51) Int. Cl.
   *G01V 5/00*     (2006.01)
   *A61B 6/03*     (2006.01)
   *G01N 23/046*   (2018.01)
   *G01T 1/29*     (2006.01)
   *A61B 6/14*     (2006.01)

(52) U.S. Cl.
   CPC ......... *A61B 6/4233* (2013.01); *G01N 23/046* (2013.01); *G01T 1/247* (2013.01); *G01T 1/2928* (2013.01); *G01V 5/0025* (2013.01); *A61B 6/14* (2013.01); *A61B 6/502* (2013.01)

(56) References Cited

U.S. PATENT DOCUMENTS

2015/0265227 A1* 9/2015 Sano ............... A61B 6/542
                                                378/64
2016/0045176 A1* 2/2016 Kimura ............ A61B 6/4233
                                                378/19

FOREIGN PATENT DOCUMENTS

WO    2014175458 A1    10/2014
WO    2016161544 A1    10/2016

\* cited by examiner

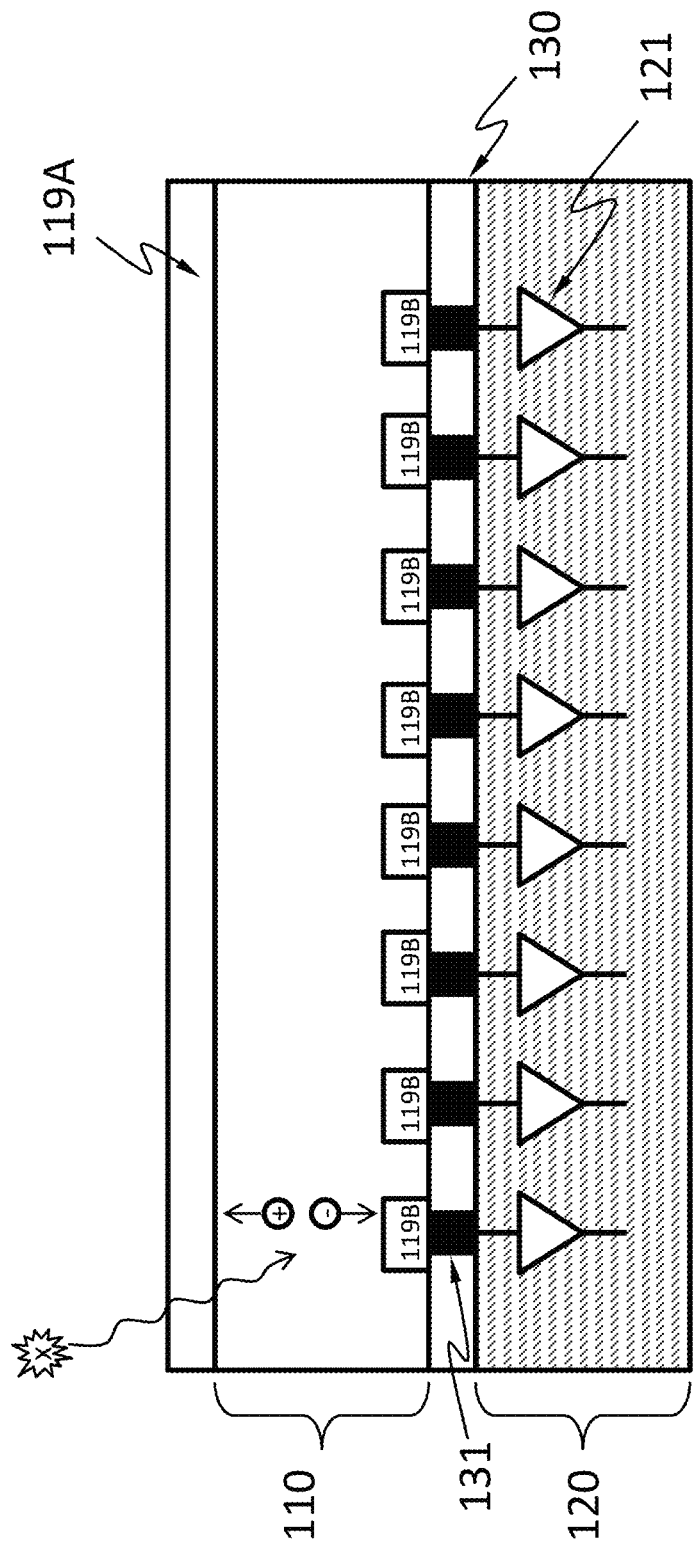

RADIATION DETECTOR

TECHNICAL FIELD

The disclosure herein relates to radiation detectors, particularly relates to semiconductor X-ray detectors.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or γ-ray. The radiation may be of other types such as α-rays and β-rays.

One type of radiation detectors is based on interaction between the radiation and a semiconductor. For example, a radiation detector of this type may have a semiconductor layer that absorbs the radiation and generate charge carriers (e.g., electrons and holes) and circuitry for detecting the charge carriers.

SUMMARY

Disclosed herein is a radiation detector, comprising: a radiation absorption layer comprising an electrode; a voltage comparator configured to compare a voltage of the electrode to a first threshold; a counter configured to register a number of photons of radiation absorbed by the radiation absorption layer; a controller; a voltmeter; wherein the controller is configured to start a time delay from a time at which the voltage comparator determines that an absolute value of the voltage equals or exceeds an absolute value of the first threshold; wherein the controller is configured to cause the voltmeter to measure the voltage upon expiration of the time delay; wherein the controller is configured to determine the number of photons by dividing the voltage measured by the voltmeter by a voltage that a single photon would have caused on the electrode; wherein the controller is configured to cause the number registered by the counter to increase by the number of photons.

According to an embodiment, the radiation detector further comprises a capacitor module electrically connected to the electrode, wherein the capacitor module is configured to collect charge carriers from the electrode.

According to an embodiment, the controller is configured to connect the electrode to an electrical ground.

According to an embodiment, the controller is configured to deactivate the voltage comparator at a beginning of the time delay.

According to an embodiment, the first threshold is 5-10% of a voltage a single photon generates on the electrode.

According to an embodiment, the radiation absorption layer comprises a diode.

According to an embodiment, the radiation absorption layer comprises silicon, germanium, GaAs, CdTe, CdZnTe, or a combination thereof.

According to an embodiment, the apparatus does not comprise a scintillator.

According to an embodiment, the apparatus comprises an array of pixels.

Disclosed herein is a system comprising any of the radiation detectors above and an X-ray source, wherein the system is configured to perform X-ray radiography on human chest or abdomen.

Disclosed herein is a system comprising any of the radiation detectors above and an X-ray source, wherein the system is configured to perform X-ray radiography on human mouth.

Disclosed herein is a cargo scanning or non-intrusive inspection (NII) system comprising any of the radiation detectors above and an X-ray source, wherein the cargo scanning or non-intrusive inspection (NII) system is configured to form an image using backscattered X-ray.

Disclosed herein is a cargo scanning or non-intrusive inspection (NII) system comprising any of the radiation detectors above and an X-ray source, wherein the cargo scanning or non-intrusive inspection (NII) system is configured to form an image using X-ray transmitted through an object inspected.

Disclosed herein is a full-body scanner system comprising any of the radiation detectors above and an X-ray source.

Disclosed herein is an X-ray computed tomography (X-ray CT) system comprising any of the radiation detectors and an X-ray source.

Disclosed herein is an electron microscope comprising any of the radiation detectors, an electron source and an electronic optical system.

Disclosed herein is a system comprising any of the radiation detectors above, wherein the system is an X-ray telescope, or an X-ray microscopy, or wherein the system is configured to perform mammography, industrial defect detection, microradiography, casting inspection, weld inspection, or digital subtraction angiography.

Disclosed herein is a method comprising: starting a time delay from a time at which an absolute value of a voltage of an electrode of a radiation absorption layer equals or exceeds an absolute value of a first threshold; measuring the voltage upon expiration of the time delay; determine a number of photons incident on the radiation absorption layer by dividing the voltage by a voltage that a single photon would have caused on the electrode; increasing a count of X-ray photon incident on the X-ray absorption layer by the number of photons.

According to an embodiment, the method further comprises connecting the electrode to an electrical ground.

According to an embodiment, the method further comprises deactivating a first circuit at a beginning of or during the time delay.

BRIEF DESCRIPTION OF FIGURES

FIG. 2C schematically shows an alternative detailed cross-sectional view of the radiation detector.

DETAILED DESCRIPTION

Figure 1:
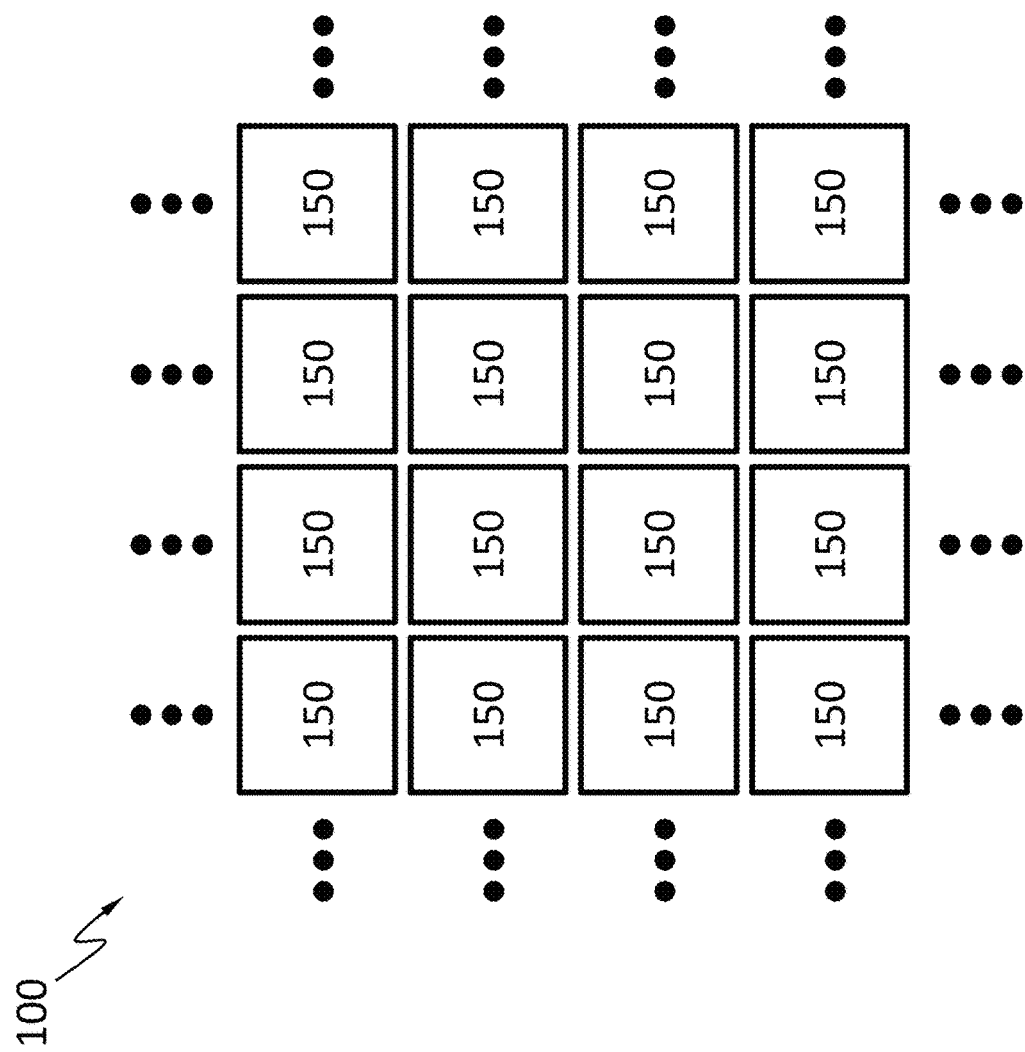
FIG. 1 schematically shows a radiation detector, according to an embodiment.

FIG. 1 schematically shows a radiation detector 100, as an example. The radiation detector 100 has an array of pixels 150. The array may be a rectangular array, a honeycomb array, a hexagonal array or any other suitable array. Each pixel 150 is configured to detect radiation from a radiation source incident thereon and may be configured measure a characteristic (e.g., the energy of the particles, the wavelength, and the frequency) of the radiation. For example, each pixel 150 is configured to count numbers of photons incident thereon whose energy falls in a plurality of bins, within a period of time. All the pixels 150 may be configured to count the numbers of photons incident thereon within a plurality of bins of energy within the same period of time. When the incident photons have similar energy, the pixels 150 may be simply configured to count numbers of photons incident thereon within a period of time, without measuring the energy of the individual photons. Each pixel 150 may have its own analog-to-digital converter (ADC) configured to digitize an analog signal representing the energy of an incident photon into a digital signal, or to digitize an analog signal representing the total energy of a plurality of incident photons into a digital signal. The pixels 150 may be configured to operate in parallel. For example, when one pixel 150 measures an incident photon, another pixel 150 may be waiting for a photon to arrive. The pixels 150 may not have to be individually addressable.

Figure 2A:
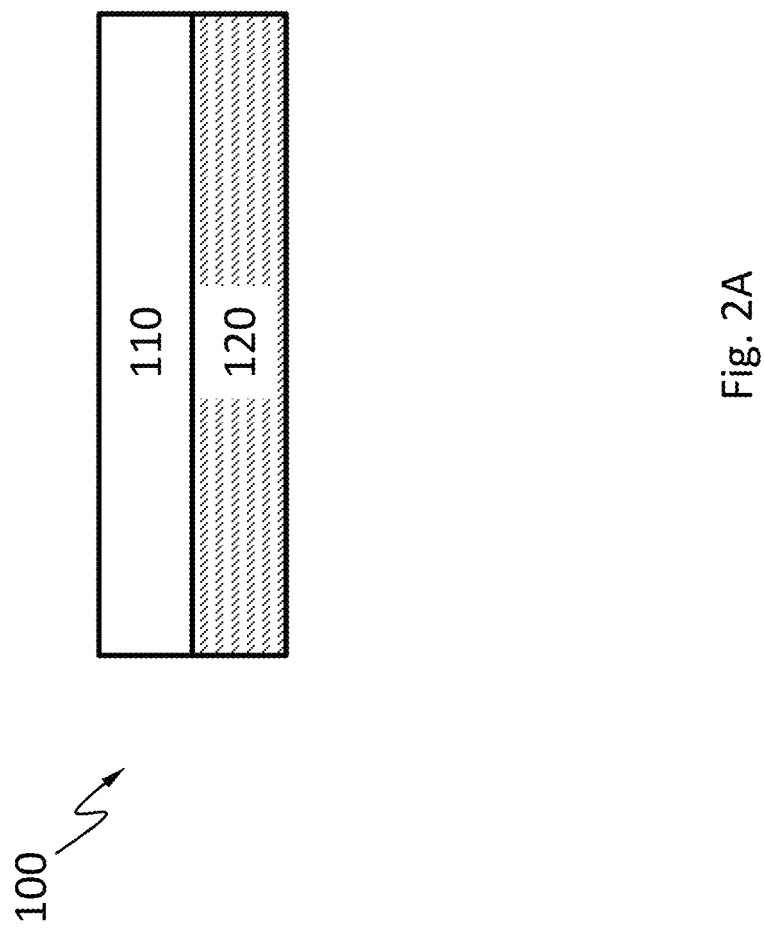
FIG. 2A schematically shows a cross-sectional view of the radiation detector.

FIG. 2A schematically shows a cross-sectional view of the radiation detector 100, according to an embodiment. The radiation detector 100 may include a radiation absorption layer 110 and an electronics layer 120 (e.g., an ASIC) for processing or analyzing electrical signals incident radiation generates in the radiation absorption layer 110. The radiation detector 100 may or may not include a scintillator. The radiation absorption layer 110 may include a semiconductor material such as, silicon, germanium, GaAs, CdTe, CdZnTe, or a combination thereof. The semiconductor may have a high mass attenuation coefficient for the radiation of interest.

Figure 2B:
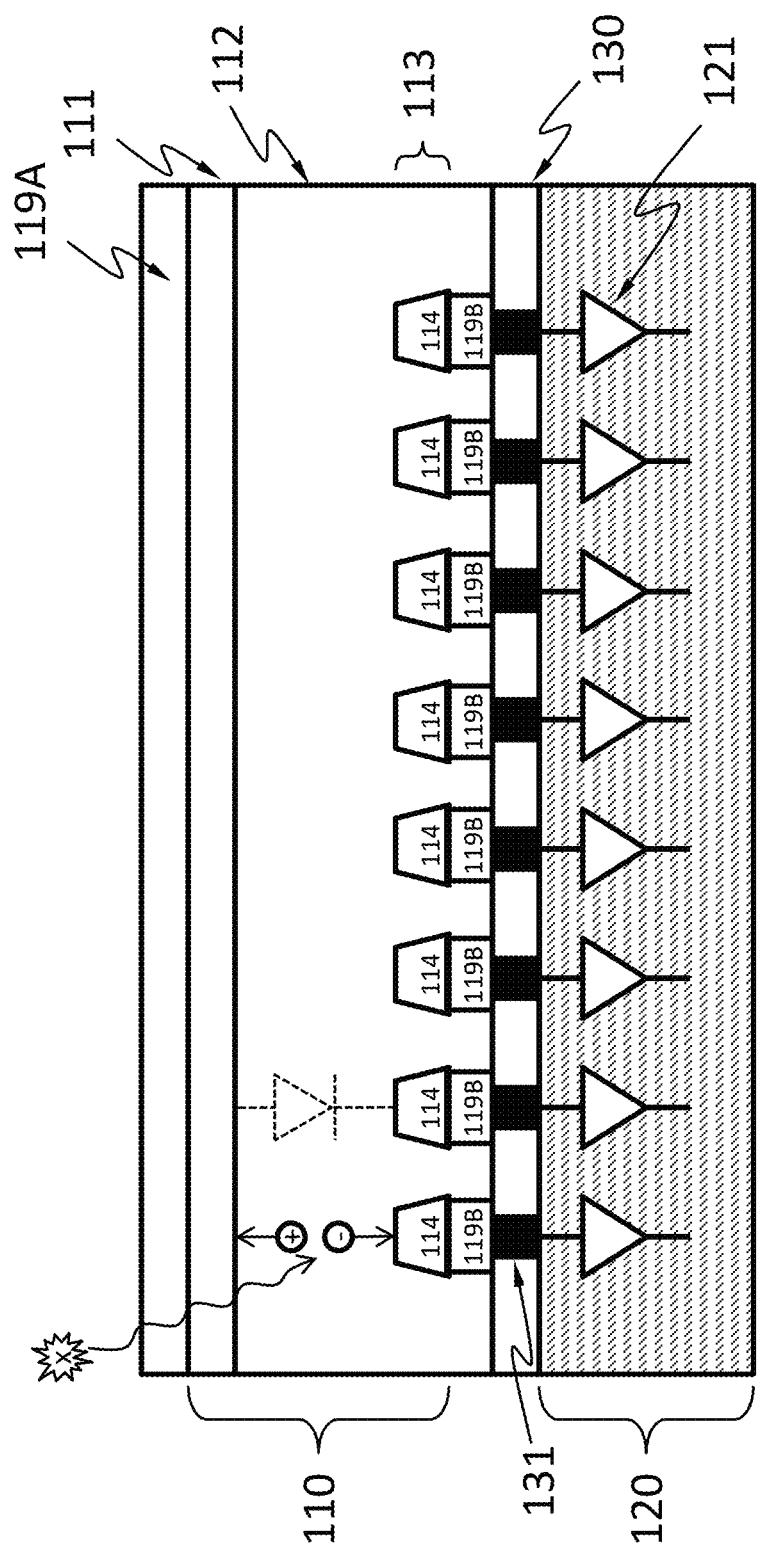
FIG. 2B schematically shows a detailed cross-sectional view of the radiation detector.

As shown in a detailed cross-sectional view of the radiation detector 100 in FIG. 2B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes having the first doped region 111 as a shared electrode. The first doped region 111 may also have discrete portions.

When radiation from the radiation source hits the radiation absorption layer 110 including diodes, the radiation photon may be absorbed and generate one or more charge carriers by a number of mechanisms. The charge carriers may drift to the electrodes of one of the diodes under an electric field. The field may be an external electric field. The electrical contact 119B may include discrete portions each of which is in electrical contact with the discrete regions 114. The term "electrical contact" may be used interchangeably with the word "electrode." In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel.

As shown in an alternative detailed cross-sectional view of the radiation detector 100 in FIG. 2C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation of interest.

When the radiation hits the radiation absorption layer 110 including a resistor but not diodes, it may be absorbed and generate one or more charge carriers by a number of mechanisms. A particle of the radiation may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessors, and memory. The electronic system 121 may include one or more ADCs. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 3A:
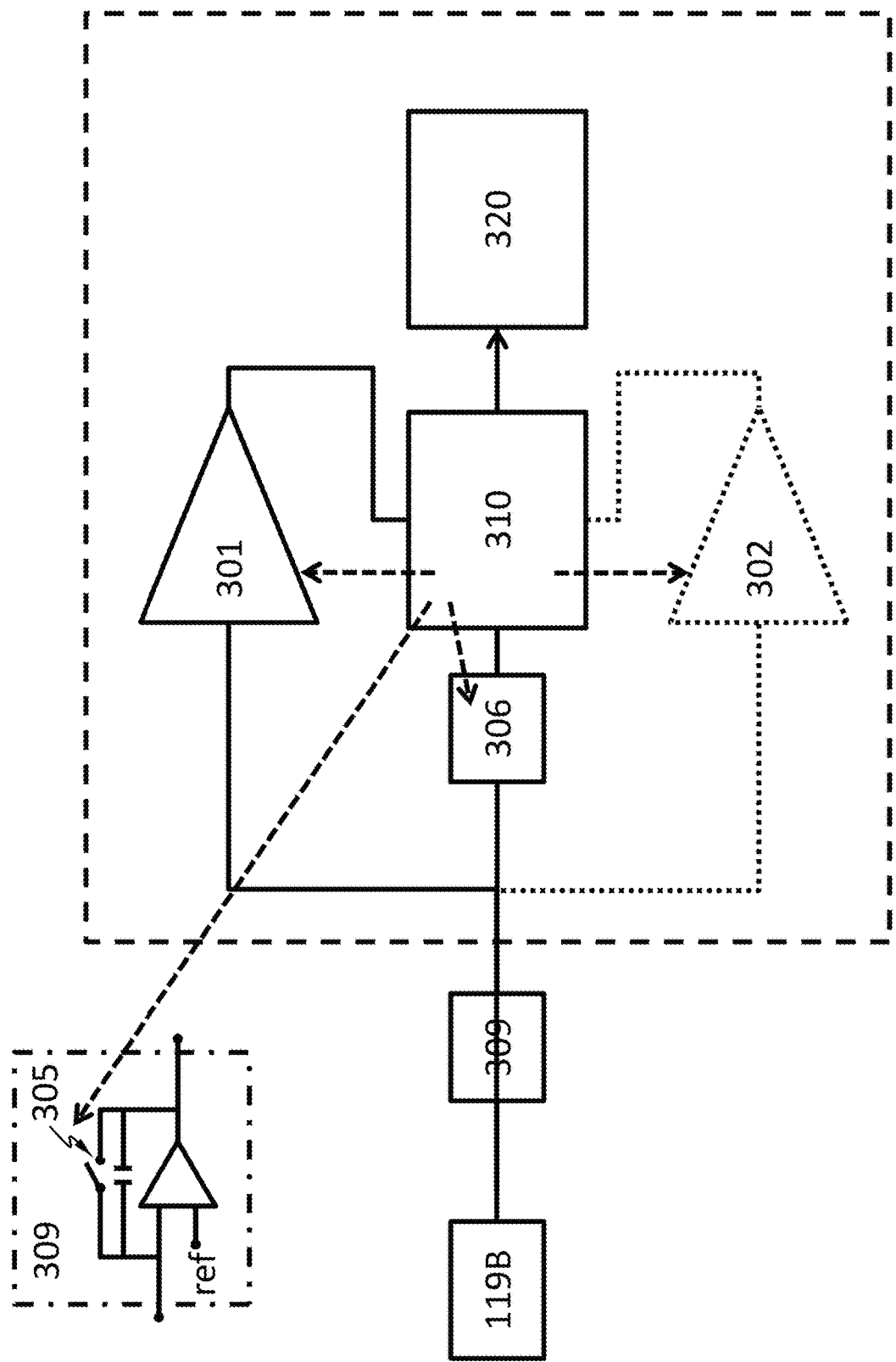
FIG. 3A and FIG. 3B each show a component diagram of an electronic system of the detector in FIG. 2B or FIG. 2C, according to an embodiment.
Figure 3B:
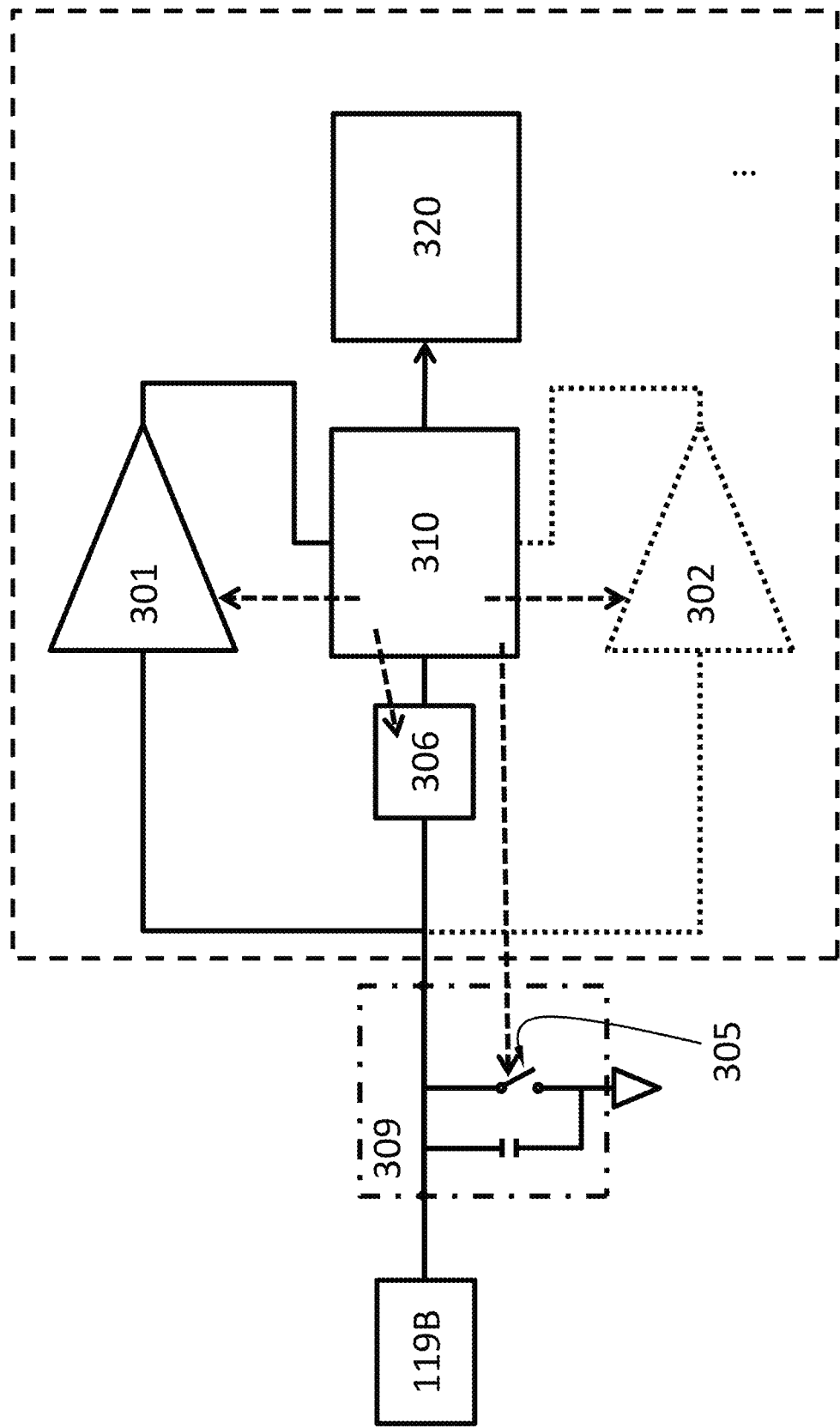

FIG. 3A and FIG. 3B each show a component diagram of the electronic system 121, according to an embodiment. The electronic system 121 may include a voltage comparator 301, a counter 320, a switch 305, a voltmeter 306 and a controller 310.

The voltage comparator 301 is configured to compare the voltage of the electrode of a diode to a first threshold. The diode may be a diode formed by the first doped region 111, one of the discrete regions 114 of the second doped region 113, and the optional intrinsic region 112. Alternatively, the voltage comparator 301 is configured to compare the voltage of an electrical contact (e.g., a discrete portion of electrical contact 119B) to a first threshold. The voltage comparator 301 may be configured to monitor the voltage directly, or calculate the voltage by integrating an electric current flowing through the diode or electrical contact over a period of time. The voltage comparator 301 may be controllably activated or deactivated by the controller 310. The voltage comparator 301 may be a continuous comparator. Namely, the voltage comparator 301 may be configured to be activated continuously, and monitor the voltage continuously. The voltage comparator 301 configured as a continuous comparator reduces the chance that the system 121 misses signals generated by an incident photon. The voltage comparator 301 configured as a continuous comparator is especially suitable when the incident radiation intensity is relatively high. The first voltage comparator 301 may be a clocked comparator, which has the benefit of lower power consumption. The first voltage comparator 301 configured as a clocked comparator may cause the system 121 to miss signals generated by some incident photons. When the incident radiation intensity is low, the chance of missing an incident photon is low because the time interval between two successive photons is relatively long. Therefore, the first voltage comparator 301 configured as a clocked comparator is especially suitable when the incident radiation intensity is relatively low. The first threshold may be 5-10%, 10%-20%, 20-30%, 30-40% or 40-50% of the voltage a single photon may generate on the electrode of the diode or the electrical contact of the resistor. The maximum voltage may depend on the energy of the incident photon, the material of the radiation absorption layer 110, and other factors. For example, the first threshold may be 50 mV, 100 mV, 150 mV, or 200 mV.

The voltage comparator 301 may include one or more op-amps or any other suitable circuitry. The voltage comparator 301 may have a high speed to allow the system 121 to operate under a high flux of incident radiation. However, having a high speed is often at the cost of power consumption.

The counter 320 is configured to register a number of photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the counter 320 and any other circuits the operation of the voltage comparator 301 does not require, before the time at which the voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the voltage comparator 301 activates the controller 310 when the absolute value of the voltage equals or exceeds the absolute value of the first threshold.

The controller 310 may be configured to cause the voltmeter 306 to measure the voltage upon expiration of the time delay. The controller 310 may be configured to connect the electrode or the electrical contact to an electrical ground, so as to reset the voltage and discharge any charge carriers accumulated on the electrode or the electrical contact. In an embodiment, the electrode or the electrical contact is connected to an electrical ground after the expiration of the time delay. In an embodiment, the electrode or the electrical contact is connected to an electrical ground for a finite reset time period. The controller 310 may connect the electrode or the electrical contact to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 4:
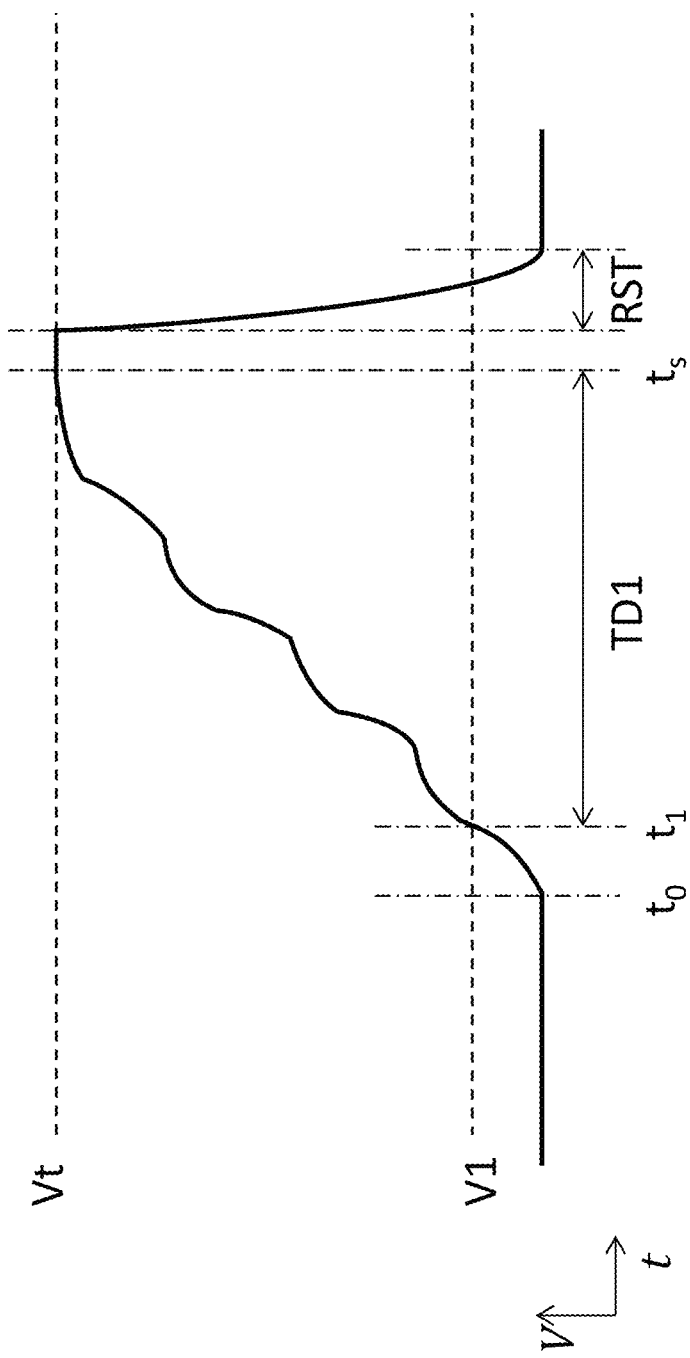
FIG. 4 schematically shows a temporal change of the voltage of the electrode or the electrical contact, caused by charge carriers generated by one or more photons incident on the diode or the resistor, according to an embodiment.

The system 121 may include a capacitor module 309 electrically connected to the electrode of the diode 300 or the electrical contact, wherein the capacitor module is configured to collect charge carriers from the electrode or the electrical contact. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode or the electrical contact accumulate on the capacitor over a period of time ("integration period") (e.g., as shown in FIG. 4, between $t_0$ to $t_1$). After the integration period has expired, the capacitor voltage is sampled and then reset by a reset switch. The capacitor module can include a capacitor directly connected to the electrode or the electrical contact.

FIG. 4 schematically shows a temporal change of the voltage of the electrode or the electrical contact, caused by charge carriers generated by one or more photons incident on the diode or the resistor, according to an embodiment. The voltage may be an integral of the electric current with respect to time. One or more photons hit the diode or the resistor starting at time to, charge carriers start being generated in the diode or the resistor, electric current starts to flow through the electrode of the diode or the electrical contact of the resistor, and the absolute value of the voltage of the electrode or the electrical contact starts to increase. At time $t_1$, the voltage comparator 301 determines that the absolute value of the voltage equals or exceeds the absolute value of the first threshold V1, and the controller 310 starts the time delay TD1 and the controller 310 may deactivate the voltage comparator 301 at the beginning of TD1. If the controller 310 is deactivated before $t_1$, the controller 310 is activated at $t_1$. At time $t_s$, the time delay TD1 expires. The photons may continue hit the diode or the resistor throughout the entirety of TD1.

The controller 310 may be configured to cause the voltmeter 306 to measure the voltage upon expiration of the time delay TD1. The voltage Vt measured by the voltmeter 306 is proportional to the amount of charge carriers generated by the incident photons from $t_0$ to $t_s$, which relates to the total energy of the incident photons. When the incident photons have similar energy, the controller 310 may be configured to determine the number of incident photons from $t_0$ to $t_s$, by dividing Vt with the voltage that a single photon would cause on the electrode or electrical contact. The controller 310 may increase the counter 320 by the number of photons.

After TD1 expires, the controller 310 connects the electrode or the electrical contact to an electric ground for a reset period RST to allow charge carriers accumulated on the electrode or the electrical contact to flow to the ground and reset the voltage. After RST, the system 121 is ready to detect another incident photon. Implicitly, the rate of incident photons the system 121 can handle in the example of FIG. 4 is limited by 1/(TD1+RST). If the voltage comparator 301 has been deactivated, the controller 310 can activate it at any time before RST expires. If the controller 310 has been deactivated, it may be activated before RST expires.

Figure 5:
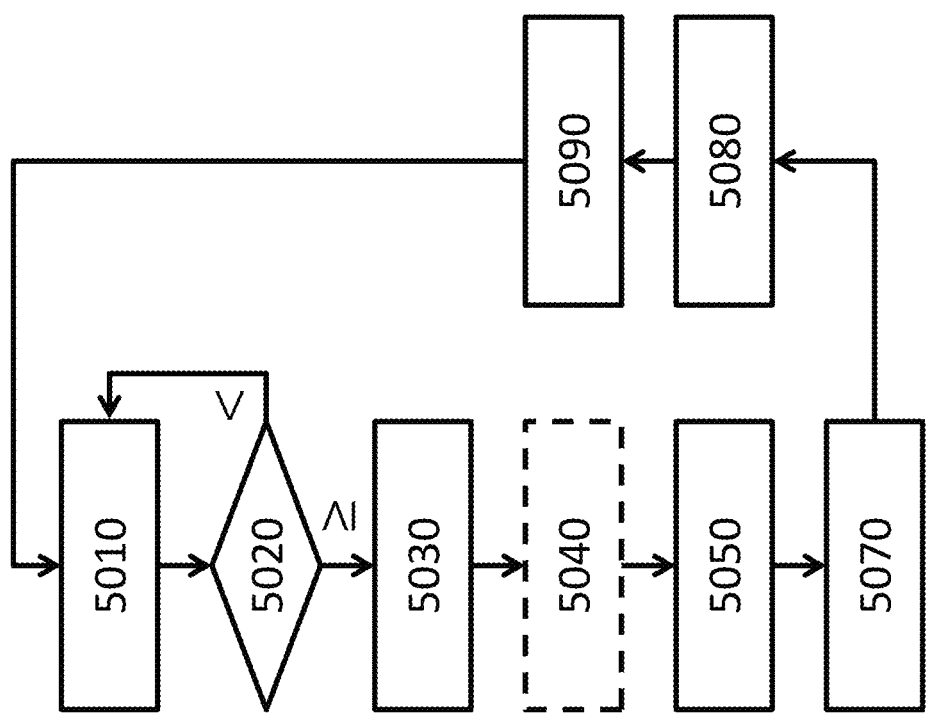
FIG. 5 shows a flow chart for a method suitable for detecting radiation using a system such as the system operating as shown in FIG. 4.

FIG. 5 shows a flow chart for a method suitable for detecting radiation using a system such as the system 121 operating as shown in FIG. 4. In procedure 5010, compare, e.g., using the voltage comparator 301, a voltage of an electrode of a diode or an electrical contact of a resistor exposed to radiation, to the first threshold. In procedure 5020, determine, e.g., with the controller 310, whether the absolute value of the voltage equals or exceeds the absolute value of the first threshold V1. If the absolute value of the voltage does not equal or exceed the absolute value of the first threshold, the method goes back to procedure 5010. If the absolute value of the voltage equals or exceeds the absolute value of the first threshold, continue to procedure 5030. In procedure 5030, start, e.g., using the controller 310, the time delay TD1. In optional procedure 5040, activate, e.g., using the controller 310, a circuit (e.g., the counter 320) during the time delay TD1 (e.g., at the expiration of TD1). In procedure 5050, measure, e.g., using the voltmeter 306, the voltage upon expiration of the time delay TD1. In procedure 5070, determine the number of photons incident on the radiation absorption layer from $t_0$ to $t_s$, by dividing the voltage measured by the voltmeter 306 by a voltage a single photon would cause on the electrode. The voltage a single photon would cause on the electrode may be known or measured separately in advance. In procedure 5080, increase the counter by the number of photons. The method goes to procedure 5090 after procedure 5080. In procedure 5090, reset the voltage to an electrical ground, e.g., by connecting the electrode of the diode or an electrical contact of a resistor to an electrical ground.

According to an embodiment, the detector 100 may use delta-sigma (sigma-delta, $\Delta\Sigma$ or $\Sigma\Delta$) modulation. In a conventional ADC, an analog signal is integrated, or sampled, with a sampling frequency and subsequently quantized in a multi-level quantizer into a digital signal. This process introduces quantization error noise. The first step in a delta-sigma modulation is delta modulation. In delta modulation the change in the signal (its delta) is encoded, rather than the absolute value. The result is a stream of pulses, as opposed to a stream of numbers. The digital output (i.e., the pulses) is passed through a 1-bit DAC and the resulting analog signal (sigma) is added to the input signal of the ADC. During the integration of the analog signal, when the analog signal reaches the delta, a counter is increased by one and the delta is deducted from the analog signal. At the end of the integration, the registered value of the counter is the digital signal and the remaining analog signal smaller than the delta is the residue analog signal.

Figure 6:
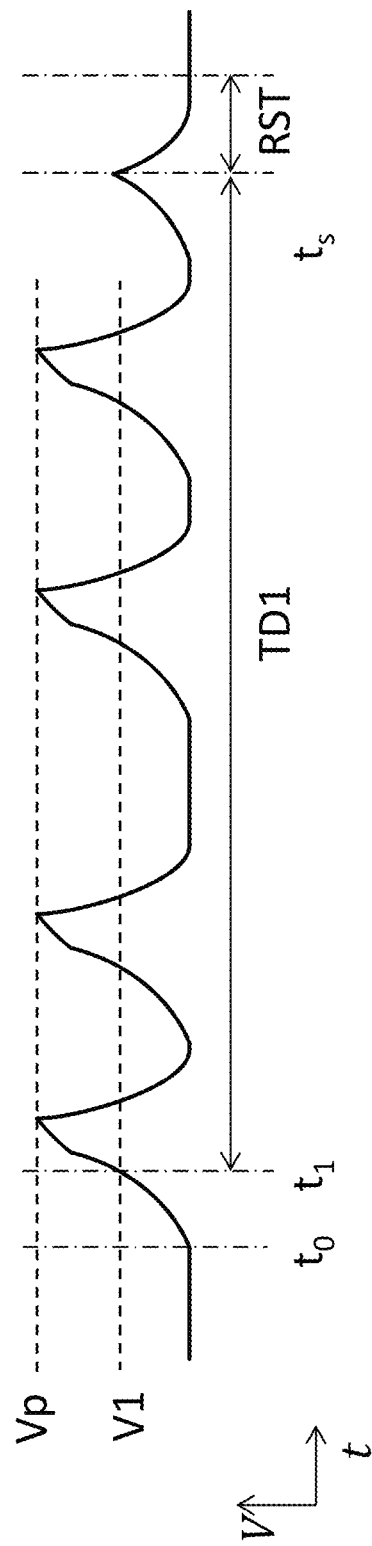
FIG. 6 schematically shows a temporal change of the voltage of the electrode or the electrical contact, caused by charge carriers generated by one or more photons incident on the diode or the resistor, according to an embodiment.

FIG. 6 schematically shows a temporal change of the voltage of the electrode or the electrical contact, caused by charge carriers generated by one or more photons incident on the diode or the resistor, according to an embodiment. The voltage may be an integral of the electric current with respect to time. At time to, one or more photons hit the diode or the resistor, charge carriers start being generated in the diode or the resistor, electric current starts to flow through the electrode of the diode or the electrical contact of the resistor, and the absolute value of the voltage of the electrode or the electrical contact starts to increase. At time $t_1$, the voltage comparator 301 determines that the absolute value of the voltage equals or exceeds the absolute value of the first threshold V1, and the controller 310 starts the time delay TD1 and the controller 310 may deactivate the voltage comparator 301 at the beginning of TD1. If the controller 310 is deactivated before $t_1$, the controller 310 is activated at $t_1$. At time $t_s$, the time delay TD1 expires.

The electronic system 121 may further include another voltage comparator 302 but omit the voltmeter 306, as shown in FIGS. 3A and 3B. During TD1, whenever the voltage comparator 302 determines that the voltage reaches Vp, which is the voltage a single incident photon would have caused on the electrode or the electrical contact, the controller 310 connects the electrode or the electrical contact to an electric ground to allow charge carriers accumulated on the electrode or the electrical contact to flow to the ground and reset the voltage and increase the counter 320 by one. After TD1 expires, the controller 310 again connects the electrode or the electrical contact to an electric ground for a reset period RST to allow charge carriers accumulated on the electrode or the electrical contact to flow to the ground and reset the voltage. The number of the counter 320 at the expiration of TD1 represents the number of incident photons from to to the expiration of TD1.

Figure 7:
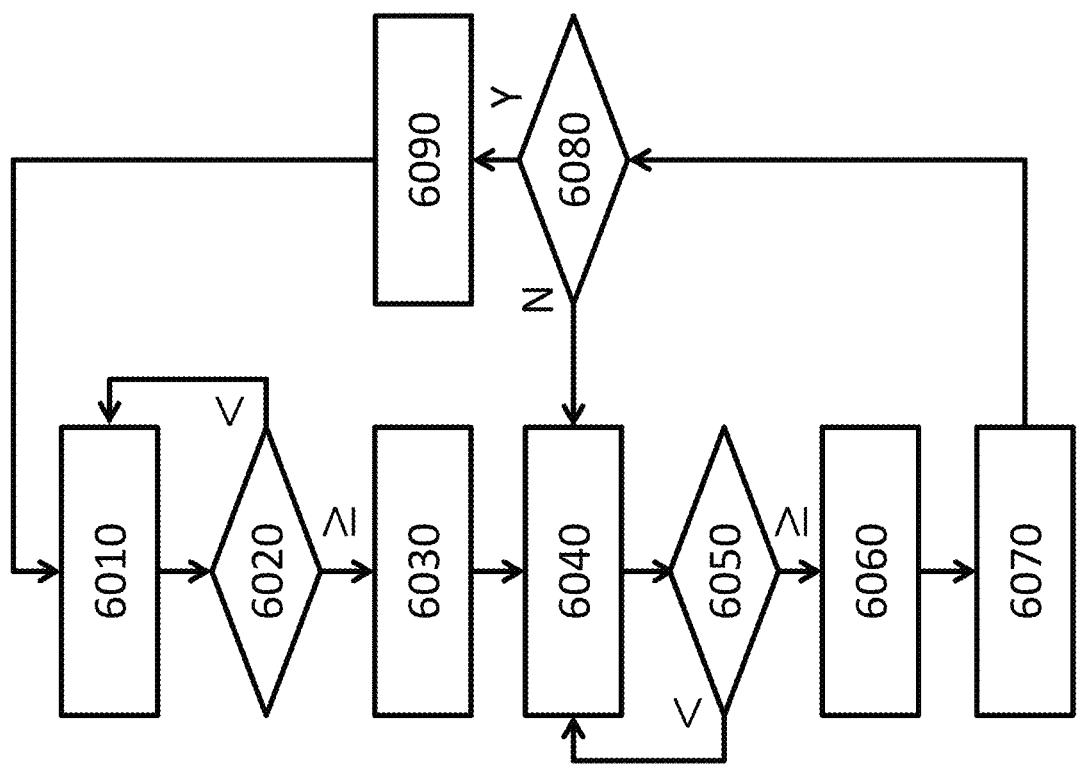
FIG. 7 shows a flow chart for a method suitable for detecting radiation using a system such as the system operating as shown in FIG. 6.

FIG. 7 shows a flow chart for a method suitable for detecting radiation using a system such as the system 121 operating as shown in FIG. 6. In procedure 6010, compare, e.g., using the voltage comparator 301, a voltage of an electrode of a diode or an electrical contact of a resistor exposed to radiation, to the first threshold. In procedure 6020, determine, e.g., with the controller 310, whether the absolute value of the voltage equals or exceeds the absolute value of the first threshold V1. If the absolute value of the voltage does not equal or exceed the absolute value of the first threshold, the method goes back to procedure 6010. If the absolute value of the voltage equals or exceeds the absolute value of the first threshold, continue to procedure 6030. In procedure 6030, start, e.g., using the controller 310, the time delay TD1. In procedure 6040, compare, e.g., using the voltage comparator 302, the voltage to a third threshold Vp, which is the voltage a single incident photon would have caused on the electrode or the electrical contact. In procedure 6050, determine, e.g., with the controller 310, whether the absolute value of the voltage reaches the absolute value of the third threshold Vp. If the absolute value of the voltage does not reach the absolute value of the threshold, the method goes back to procedure 6040. If the absolute value of the voltage reaches the absolute value of the third threshold, continue to procedure 6060. In procedure 6060, increase the counter by one. In procedure 6070, reset the voltage to an electrical ground, e.g., by connecting the electrode of the diode or an electrical contact of a resistor to an electrical ground. In procedure 6080, determine whether the time delay TD1 has expired. If it has not, the flow goes back to procedure 6040. If it has, the flow goes to procedure 6090, where the voltage is reset to an electrical ground.

Figure 8:
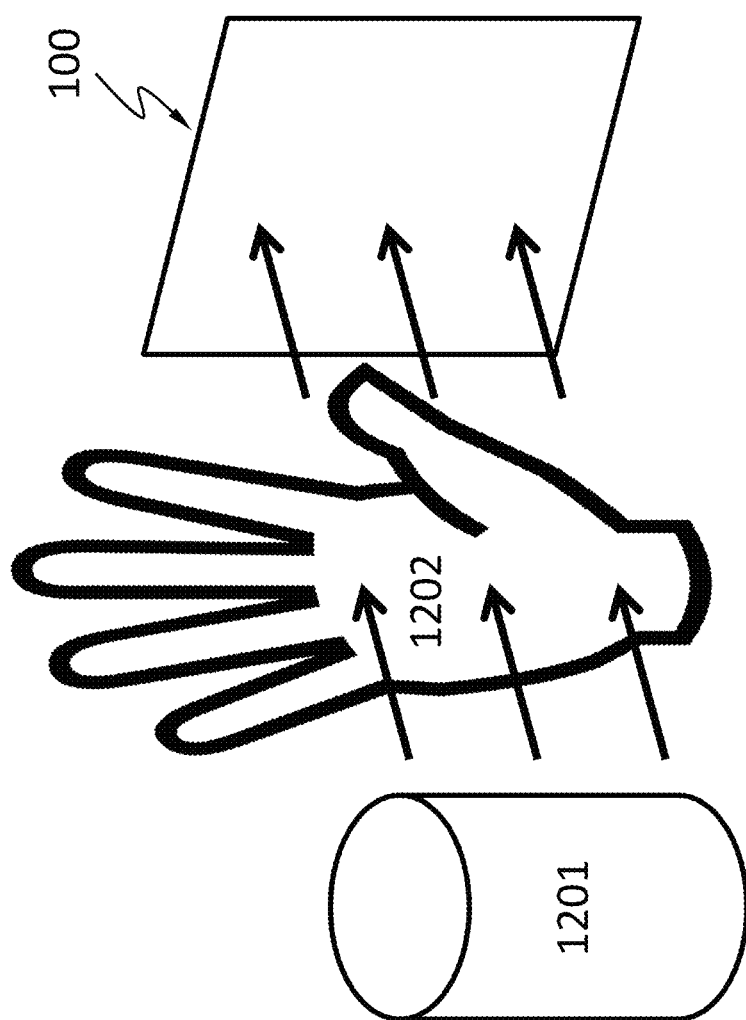
FIG. 8 schematically shows a system comprising the radiation detector described herein, suitable for medical imaging such as chest X-ray radiography, abdominal X-ray radiography, etc., according to an embodiment FIG. 9 schematically shows a system comprising the radiation detector described herein suitable for dental X-ray radiography, according to an embodiment.

FIG. 8 schematically shows a system comprising the radiation detector 100 described herein. The system may be used for medical imaging such as chest X-ray radiography, abdominal X-ray radiography, etc. The system comprises an X-ray source 1201. X-ray emitted from the X-ray source 1201 penetrates an object 1202 (e.g., a human body part such as chest, limb, abdomen), is attenuated by different degrees by the internal structures of the object 1202 (e.g., bones, muscle, fat and organs, etc.), and is projected to the radiation detector 100. The radiation detector 100 forms an image by detecting the intensity distribution of the X-ray.

Figure 9:
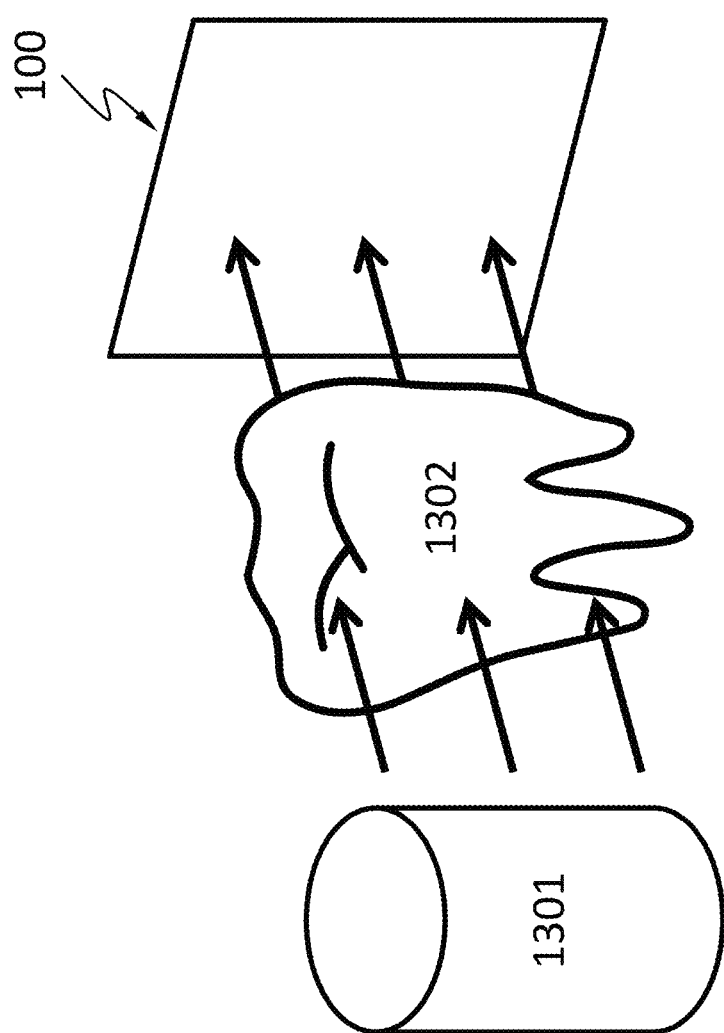

FIG. 9 schematically shows a system comprising the radiation detector 100 described herein. The system may be used for medical imaging such as dental X-ray radiography. The system comprises an X-ray source 1301. X-ray emitted from the X-ray source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the radiation detector 100. The radiation detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 10:
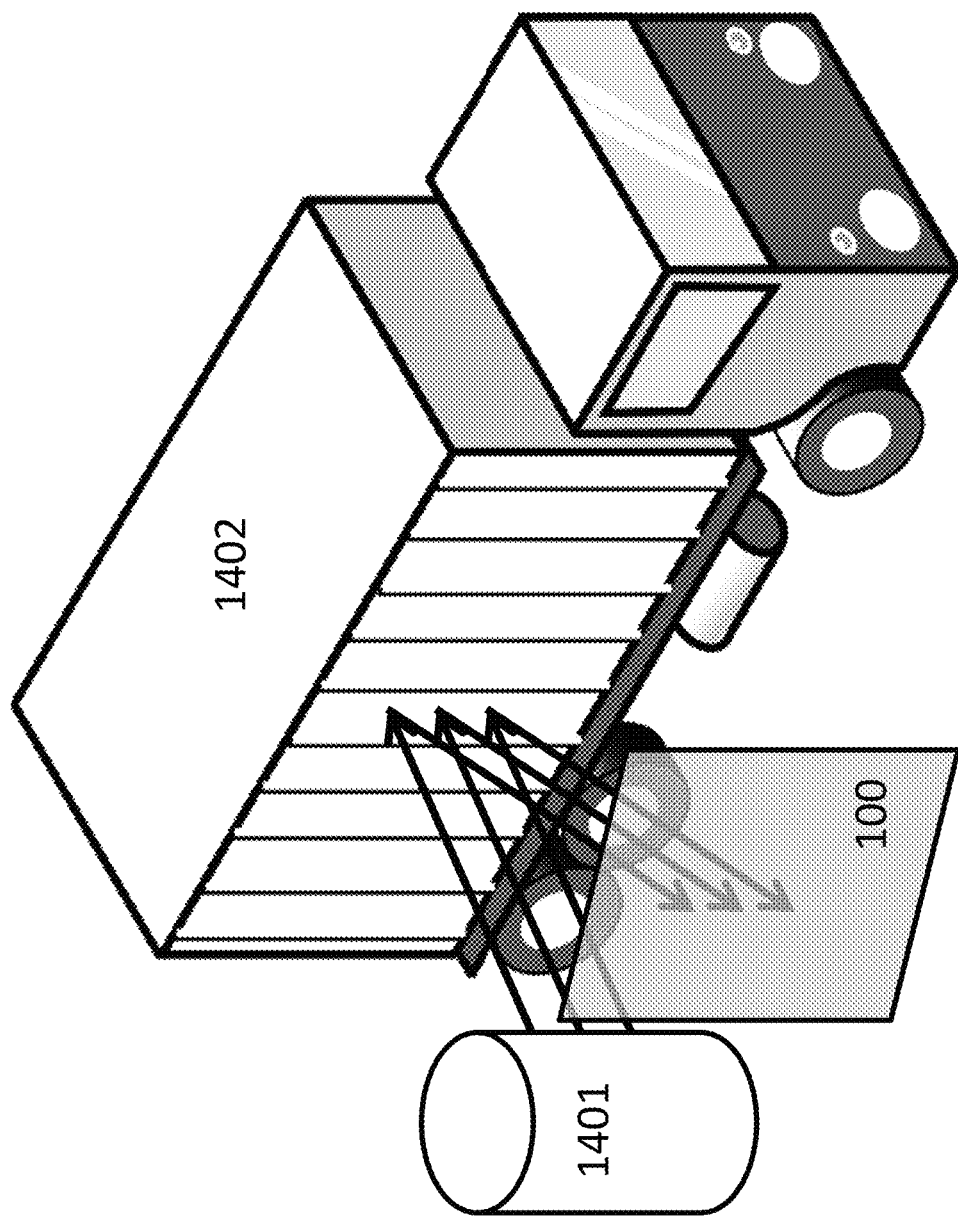
FIG. 10 schematically shows a cargo scanning or non-intrusive inspection (NII) system comprising the radiation detector described herein, according to an embodiment.

FIG. 10 schematically shows a cargo scanning or non-intrusive inspection (NII) system comprising the radiation detector 100 described herein. The system may be used for inspecting and identifying goods in transportation systems such as shipping containers, vehicles, ships, luggage, etc. The system comprises an X-ray source 1401. X-ray emitted from the X-ray source 1401 may backscatter from an object 1402 (e.g., shipping containers, vehicles, ships, etc.) and be projected to the radiation detector 100. Different internal structures of the object 1402 may backscatter X-ray differently. The radiation detector 100 forms an image by detecting the intensity distribution of the backscattered X-ray and/or energies of the backscattered X-ray photons.

Figure 11:
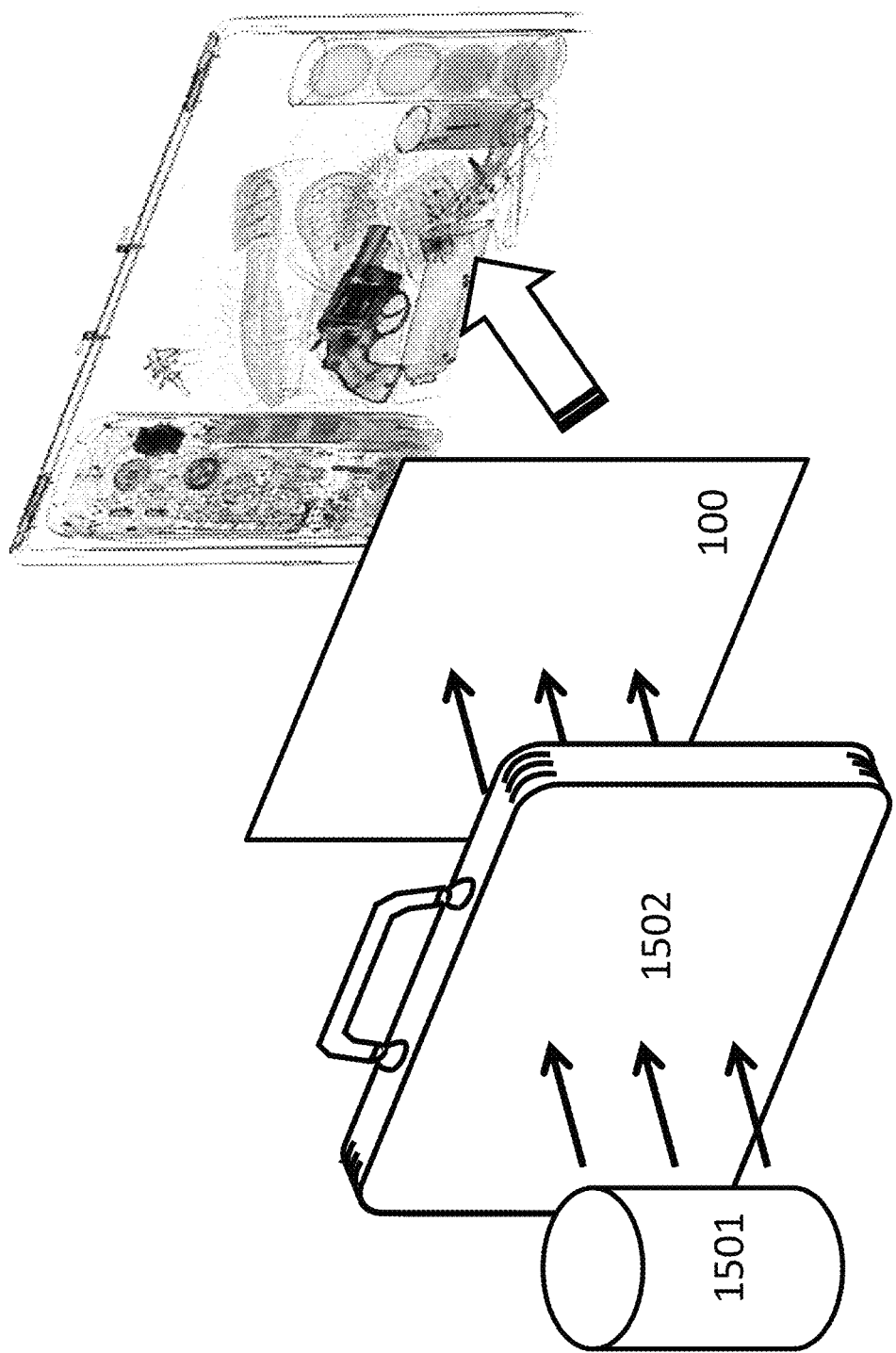
FIG. 11 schematically shows another cargo scanning or non-intrusive inspection (NII) system comprising the radiation detector described herein, according to an embodiment.

FIG. 11 schematically shows another cargo scanning or non-intrusive inspection (NII) system comprising the radiation detector 100 described herein. The system may be used for luggage screening at public transportation stations and airports. The system comprises an X-ray source 1501. X-ray emitted from the X-ray source 1501 may penetrate a piece of luggage 1502, be differently attenuated by the contents of the luggage, and projected to the radiation detector 100. The radiation detector 100 forms an image by detecting the intensity distribution of the transmitted X-ray. The system may reveal contents of luggage and identify items forbidden on public transportation, such as firearms, narcotics, edged weapons, flammables.

Figure 12:
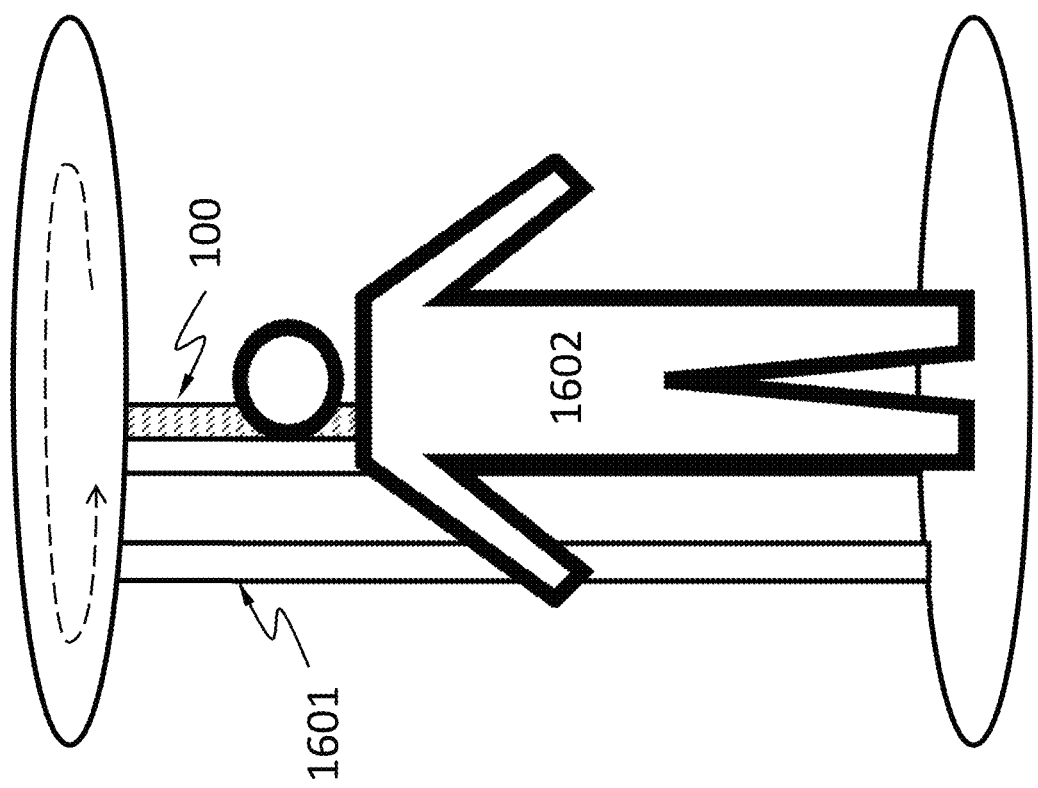
FIG. 12 schematically shows a full-body scanner system comprising the radiation detector described herein, according to an embodiment.

FIG. 12 schematically shows a full-body scanner system comprising the radiation detector 100 described herein. The full-body scanner system may detect objects on a person's body for security screening purposes, without physically removing clothes or making physical contact. The full-body scanner system may be able to detect non-metal objects. The full-body scanner system comprises an X-ray source 1601. X-ray emitted from the X-ray source 1601 may backscatter from a human 1602 being screened and objects thereon, and be projected to the radiation detector 100. The objects and the human body may backscatter X-ray differently. The radiation detector 100 forms an image by detecting the intensity distribution of the backscattered X-ray. The radiation detector 100 and the X-ray source 1601 may be configured to scan the human in a linear or rotational direction.

Figure 13:
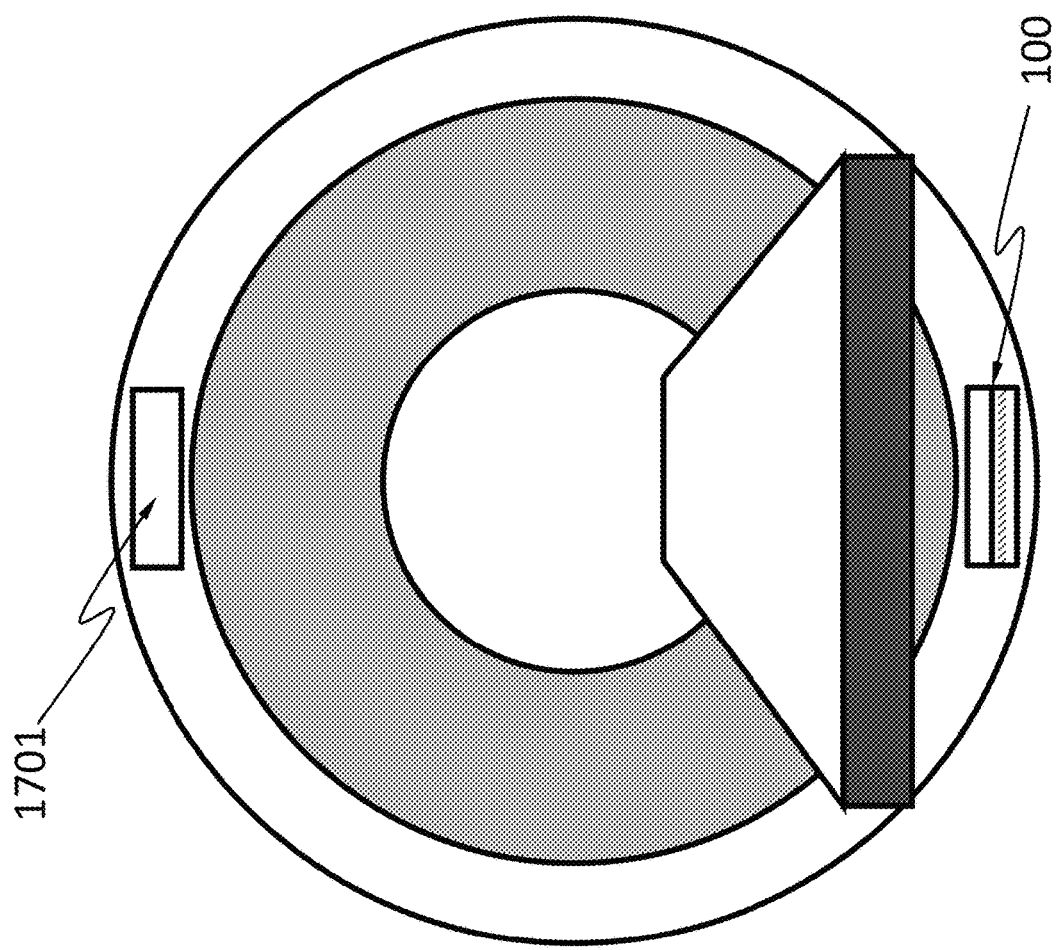
FIG. 13 schematically shows an X-ray computed tomography (X-ray CT) system comprising the radiation detector described herein, according to an embodiment.

FIG. 13 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the radiation detector 100 described herein and an X-ray source 1701. The radiation detector 100 and the X-ray source 1701 may be configured to rotate synchronously along one or more circular or spiral paths.

Figure 14:
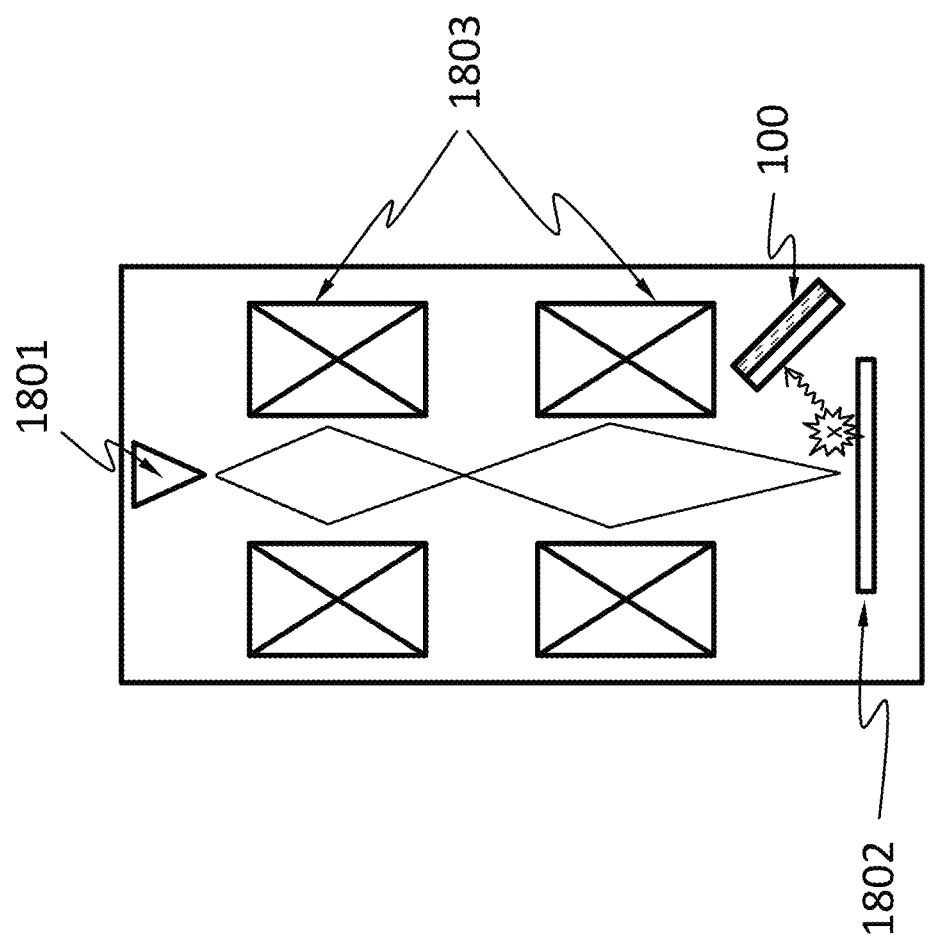
FIG. 14 schematically shows an electron microscope comprising the radiation detector described herein, according to an embodiment.

FIG. 14 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the radiation detector 100 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the radiation detector 100.

The radiation detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 100 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A radiation detector, comprising:
   a radiation absorption layer comprising an electrode;
   a voltage comparator configured to compare a voltage of the electrode to a first threshold;
   a counter configured to register a number of photons of radiation absorbed by the radiation absorption layer;
   a controller;
   a voltmeter;
   wherein the controller is configured to start a time delay from a time at which the voltage comparator determines that an absolute value of the voltage equals or exceeds an absolute value of the first threshold;
   wherein the controller is configured to cause the voltmeter to measure the voltage upon expiration of the time delay;
   wherein the controller is configured to determine a number of photons by dividing the voltage measured by the voltmeter by a voltage that a single photon would have caused on the electrode;
   wherein the controller is configured to cause the number registered by the counter to increase by the number of photons.

2. The radiation detector of claim 1, further comprising a capacitor module electrically connected to the electrode, wherein the capacitor module is configured to collect charge carriers from the electrode.

3. The radiation detector of claim 1, wherein the controller is configured to connect the electrode to an electrical ground.

4. The radiation detector of claim 1, wherein the controller is configured to deactivate the voltage comparator at a beginning of the time delay.

5. The radiation detector of claim 1, wherein the first threshold is 5-10% of a voltage a single photon generates on the electrode.

6. The radiation detector of claim 1, wherein the radiation absorption layer comprises a diode.

7. The radiation detector of claim 1, wherein the radiation absorption layer comprises silicon, germanium, GaAs, CdTe, CdZnTe, or a combination thereof.

8. The radiation detector of claim 1, wherein the apparatus does not comprise a scintillator.

9. The radiation detector of claim 1, wherein the apparatus comprises an array of pixels.

10. A system comprising the radiation detector of claim 1 and an X-ray source, wherein the system is configured to perform X-ray radiography on human chest or abdomen.

11. A system comprising the radiation detector of claim 1 and an X-ray source, wherein the system is configured to perform X-ray radiography on human mouth.

12. A cargo scanning or non-intrusive inspection (NII) system, comprising the radiation detector of claim 1 and an X-ray source, wherein the cargo scanning or non-intrusive inspection (NII) system is configured to form an image using backscattered X-ray.

13. A cargo scanning or non-intrusive inspection (NII) system, comprising the radiation detector of claim 1 and an X-ray source, wherein the cargo scanning or non-intrusive inspection (NII) system is configured to form an image using X-ray transmitted through an object inspected.

14. A full-body scanner system comprising the radiation detector of claim 1 and an X-ray source.

15. An X-ray computed tomography (X-ray CT) system comprising the radiation detector of claim 1 and an X-ray source.

16. An electron microscope comprising the radiation detector of claim 1, an electron source and an electronic optical system.

17. A system comprising the radiation detector of claim 1, wherein the system is an X-ray telescope, or an X-ray microscopy, or wherein the system is configured to perform mammography, industrial defect detection, microradiography, casting inspection, weld inspection, or digital subtraction angiography.

18. A method comprising:
    starting a time delay from a time at which an absolute value of a voltage of an electrode of a radiation absorption layer equals or exceeds an absolute value of a first threshold;
    measuring the voltage upon expiration of the time delay;
    determine a number of photons incident on the radiation absorption layer by dividing the voltage by a voltage that a single photon would have caused on the electrode;
    increasing a count of X-ray photon incident on the X-ray absorption layer by the number of photons.

19. The method of claim 18, further comprising connecting the electrode to an electrical ground.

20. The method of claim 18, further comprising deactivating a first circuit at a beginning of or during the time delay.

\* \* \* \* \*